United States Patent [19]

Richardson

[11] Patent Number: 4,473,574

[45] Date of Patent: Sep. 25, 1984

[54] PROPHYLAXIS OF ARTERIAL DISEASE

[75] Inventor: Brian P. Richardson, Magden, Switzerland

[73] Assignee: Sandoz Ltd., Basel, Switzerland

[21] Appl. No.: 461,223

[22] Filed: Jan. 26, 1983

[30] Foreign Application Priority Data

Feb. 1, 1982 [GB] United Kingdom ............... 8202780

[51] Int. Cl.$^3$ ............................................. A61K 31/44
[52] U.S. Cl. .................................................. 424/263
[58] Field of Search ............................. 424/263, 267

[56] References Cited

U.S. PATENT DOCUMENTS 3,838,125  9/1974  Schenker ........................... 544/236

Primary Examiner—Stanley J. Friedman
Attorney, Agent, or Firm—Gerald D. Sharkin; Robert S. Honor; Thomas O. McGovern

[57] ABSTRACT

A method for the prophylaxis of inflammatory, degenerative or proliferative arterial disease which method comprises administering an effective amount of endralazine.

13 Claims, No Drawings

PROPHYLAXIS OF ARTERIAL DISEASE

The present invention relates to a novel method for the prophylaxis of arterial disease, in particular of arterial disease characterised by inflammation, degeneration and/or proliferation of the arterial tissues.

Various proposals have been made for the treatment of arterial disease of the above indicated type. In general, treatment today is based on compounds which lower the lipid concentrations in the blood, see e.g. Chapter 34 in Goodmann and Gilman's The Pharmacological Basis of Therapeutics, 6th Edition, 1980. The treatment of arterial disease is still not satisfactory. The finding of new methods for their direct treatment, and for preventing further deterioration of the arterial tissue, remains a major objective.

In accordance with the present invention it has now surprisingly been found that the progression of inflammatory, degenerative and proliferative arterial disease, for example Polyarteritis nodosa and arteriosclerosis, may be prevented by the administration of endralazine.

Endralazine is 6-benzoyl-3-hydrazine-5,6,7,8-tetrahydropyrido(9,3-c)pyrodazine, and is hereinafter referred to as the compound of the invention.

Its preparation is known from U.S. Pat. No. 3,838,125. It is a potent peripheral vasodilator useful in the treatment of hypertension. It is commercially available under the name MIRETILAN. The compound of the invention may be administered in free base form or in pharmaceutically acceptable acid addition salt form, preferably the mesylate. The pharmacological properties of the compound of the invention are described in detail in R. Salzmann et al. Arzneimittelforschung, 29(11) 1843-1853 (1979).

Until now however there has been no report indicating that the compound of the invention is effective in preventing the progressive development (i.e. is effective in the prophylaxis) of arteriosclerosis per se. It will accordingly be appreciated that the present invention derives from the surprising and unexpected finding that the compound of the invention acts directly to prevent progressive degeneration and necrosis of arterial tissue characteristic of inflammatory, degenerative and proliferative arterial disease and is accordingly useful in the prophylaxis of such disease, in particular in the prophylaxis of arteriosclerosis and Polyarteritis nodosa, as indicated in the test methods described in the following examples. The present invention accordingly provides a means for the prophylaxis, in particular the long-term prophylaxis, of causal arterial disease rather than the symptomatic treatment or alleviation of associated conditions.

In accordance with the foregoing the present invention provides, in a first aspect, a method for the prophylaxis of inflammatory, degenerative and proliferative arterial disease comprising administering an effective amount of the compound of the invention.

Particular diseases which may be treated in accordance with the method of the invention include Polyarteritis nodosa and arteriosclerosis. Particular varieties of arteriosclerosis susceptible to prophylaxis include decrescent, diffuse and nodular arteriosclerosis as well as cerebral and coronary arteriosclerosis.

In a further aspect the present invention also provides a method for the prevention of progressive inflammatory, degenerative or proliferative damage in arteries comprising administering an effective amount of the compound of the invention.

Such progressive damage includes for example the development of vascular lesions, such as smooth muscle proliferation, nodule and arteriosclerosic plaque formation as well as perivascular inflammatory cell infiltration.

Because of the prophylactic effect of the compound of the invention, the incidence of diseases such as thrombosis, infarction, stroke, angina pectoris, transient ischaemic attacks, senile dementia and intermittent claudication, which can arise as sequelae to inflammatory, degeneration or proliferative damage in arteries, may be minimized.

The compound for use in the method of the invention may be employed either in free base form or in pharmaceutically acceptable salt form, e.g. as the mesylate or hydrochloride.

Generally the activities of such salt forms will be of the same order as that of the free base form, and references to compounds in the free form throughout the specification and claims are to be understood as including known salt forms. Amounts of compounds recited herein however to the amount of the free form unless otherwise indicated.

The utility of the compound of the invention in the prophylaxis of inflammatory, degeneration and proliferative arterial disease or in preventing progressive inflammatory, degenerative or proliferative arterial damage is demonstrated in animal tests, e.g. in accordance with the methods described in the following trials.

TRIAL I: PROTECTIVE EFFECT AGAINST SPONTANEOUS POLYARTERITIS NODOSA IN THE RAT;

Background

Polyarteritis nodosa is a disease occurring spontaneously in rats (Wigley, N.Z. Med. J., 71,151–158, (1970)). In certain strains of rat (e.g. OFA), in particular male rats, kept under laboratory conditions it is the most frequent cause of spontaneous death. It is characterised macroscopically by enlargement and convolution of the mesenteric vessels and by the appearance of multiple aneurysmal dilations.

The detailed morphology of the disease in rats varies considerably from organ to organ. In e.g. the tests the morphology closely parallels that of the disease Polyarteritis nodosa as it occurs in man. In e.g. the mesenteric bed and renal arteries the morphology of the disease displays characteristics (e.g. vacuolisation and disorientation of arterial smooth muscle cells, hyalinization of the intimal and subintimal region, luminal occlusion and thrombosis) more clearly typical of classical arteriosclerosis, e.g. as it occurs in man. Thus on the basis of frequency of occurrence and morphology, it appears that Polyarteritis nodosa in rats may have a closer affinity to arteriosclerosis (rather than Polyarteritis nodosa) occurring in man. The study of the effects of drug administration on the progress of Polyarteritis nodosa in the rat affords a highly indicative model for determining effectiveness in the treatment of human arterial disease and in particular of both Polyarteritis nodosa and arteriosclerosis as they occur in man.

Test Method

Two hundred 8-week old albino rats (OFA Sandoz SPF; male and female) are divided equally into 1 control and 3 treated groups. Test substance, e.g. endralazine, is mixed into the feed of the treated groups at three different concentrations so as to provide a mean drug intake at a differing daily dosage rate for each group. The animals are kept in pairs under SPF conditions for the duration of the trial which lasts 2 years. During the course of the trial the test animals have free access to water and feed. Food consumption is assessed weekly and the drug concentrations adjusted as required to maintain the required daily dosage rate.

A full necropsy is carried out on all animals dying spontaneously as well as those surviving until the end of the treatment period. The latter are sacrificed by $CO_2$ inhalation.

In the above test-method it is found that the compound of the invention administered at dosages of an order appropriate for exerting a peripheral vasodilation effect, e.g. as taught in the art, causes a dose-dependent decrease in the overall number of rats dying from Polyarteritis nodosa (i.e. in which the only determinable cause of death is hemorrhage caused by Polyarteritis nodosa), and a decrease in the overall number of survivors with macroscopic evidence of the disease in the mesenteric and other abdominal arteries as determined by visual inspection and palpatation at necropsy, compared with untreated controls.

| DOSE mg/kg/day | No. of rats/ group | % of spontaneous deaths resulting from Polyarteritis nodosa | % of survivors exhibiting Polyarteritis nodosa | Total % of rats with Polyarteristis nodosa |
| --- | --- | --- | --- | --- |
| 0 (control) | 99 | 28.8 | 30 | 29.3 |
| 3 | 99 | 20.6 | 17.1 | 19.4 |
| 21 | 100 | 9.1 | 17.6 | 12.0** |
| 149 | 98 | 0.0* | 2.8** | 1.0*** |

*P less than 0.05,
**P less than 0.01,
***P less than 0.001, versus Controls

TRIAL 2: ARTERIOSCLEROSIS IN THE RAT

Background

Although Polyarteritis nodosa is the most common cause of spontaneous death in male rats, e.g. of the OFA strain, kept under laboratory conditions, lesions characteristic of Polyarteritis nodosa (e.g. fibrinoid necrosis and perivascular cell infiltration) rarely occur in the heart, even in the case of animals severely affected by the disease. In the heart lesions are almost exclusively attributable to classical arteriosclerosis and include, in addition to those recited in the background introduction to Trial 1, classical arteriosclerotic plaques with cholesterol clefts. The rat heart accordingly provides a model for directly indicating effectiveness of drug administration in the treatment and prevention of arteriosclerosis. The protective effect of the compound of the invention against arteriosclerosis may be confirmed in the following test:

Test Method

The study may be carried out using groups of control and treated rats maintained for a two year trial period as previously described for Example 1. Hearts from all animals, i.e. both those dying spontaneously and those sacrificed at the end of the two year trial period, may be taken at necropsy and preserved in 4% buffered formaldehyde. For examination the hearts may be cut transversally at the level of the left papillary muscle and the candal portion (i.e. the ventricles) is embedded in paraplast.

Histological sections are cut to a thickness of 5 microns and stained with aldehyde fuchsin. The degree of stenosis of the left and right descending coronary arteries, as caused by the presence of occluding arteriosclerotic lesions, is quantified in a minimum of 4 histological sections for each rat. This is done by projecting the microscopic images of these arteries onto the measuring tablet of a semiautomatic image analyzer (MOP AM-02, Kontron) interfaced with a table computer (HP-9815 A-001, Hewlett-Packard). The circumference of the internal elastic lamina in each case is measured automatically with the image analyzer and registered as 100%.

The circumference of the lumen of the artery is then measured and expressed as a percentage of the circumference of the internal elastic lamina. This is the so-called "percentage coronary patency". The percentage occlusion is then simply 100 minus the percentage coronary patency. Since arteriosclerotic lesions occur in a local fashion rather than being uniformly distributed along the length of the artery, the highest degree of occlusion found in any of the descending coronary arteries (i.e. "worst score") is the value taken for each animal and used for statistical analysis. The mean "worst score" for control and treated groups individually is then calculated and compared statistically using the Mann-Whitney U-Test.

The compound of the invention may be administered to subjects suffering from arterial disease. Indications of arterial disease are well known, e.g. transient ischaemic attacks, infarction and angina pectoris. Such arterial disease may be detected by non-invasive techniques, for example ultrasound or nuclear magnetic resonance. The compound may alternatively be administered to subjects thought to possess high risk factors for arteriosclerosis, e.g. hyperlipidaemia.

The amount of compound administered in practising the method of the invention will, of course, vary according the mode of administration, the condition to be treated and the therapy desired.

In general, satisfactory results are obtained on administration at dosages comparable with those known for use of the compound as an anti-hypertensive agent, and as taught in the art, for example in the literature hereinbefore referred to.

In general, the dosage will be in the range of from about 0.5 to 150 mg/kg animal body weight per day. Conveniently the compound is presented in unit dosage form administered 2 to 4 times daily or in sustained release form.

For the long-term prophylactic treatment of larger mammals exhibiting e.g. arteriosclerosis, the total daily dosage will in general be of the order, of from about 10 to about 600 mg, e.g. 50 to 300 mg, suitably administered in unit dosage form containing from about 2 to 300 mg or 12 to 150 mg of compound of the invention per unit dosage.

Pharmaceutical compositions for use in the method of the invention may be prepared in accordance with standard techniques, for example by admixture of the compound of the invention with conventional pharmaceutically acceptable diluents and carriers and optionally other excipients, using, e.g., dry granulating techniques as endralazine is water-sensitive.

Suitable forms for administration include tablets and capsules. Solid forms suitable for oral administration are preferred.

Tablets may contain the compound of the invention in admixture with conventional pharmaceutically acceptable excipients, such as calcium sulphate, dried corn starch, magnesium stearate, silica, polyvinylpyrrolidone, etc.

The tablets may be uncoated or coated by known techniques. Sustained release forms, e.g. endralazine mesylate embedded in a wax matrix of hydrogenated castor oil and paraffin, to delay disintegration and absorption in the gastrointestinal tract may be formulated to provide a sustained action over a long period.

If desired the pharmaceutical compositions may contain further active agents, e.g. guanifacine (see UK Specification No. 1,565,686), pindolol (see DOS No. 2,458,164), or pindolol and clopamide (see DOS No. 3,005,029).

Pharmaceutical compositions containing endralazine mesylate suitable for oral administration in accordance with the method of the invention are commercially available.

The following are illustrate of suitable compositions for administration in the method of the invention.

EXAMPLE 1

| Retard Preparation | |
|---|---|
| Constituents | mg |
| 1. Endralazine mesylate | 13.57 |
| 2. Polyvinylpyrrolidone | 2.75 |
| 3. Calcium sulphate dihydrate | 43.36 |
| 4. Corn Starch | 10.32 |
| 5. Castor wax | 15.6 |
| 6. Solid Paraffin | 3.9 |
| 7. Magnesium stearate | 0.5 |
| | 90 mg |

The first four constituents are mixed together. The constituents 5 and 6 are added and then constituent 7. The mixture is then pressed into tablets.

EXAMPLE 2

| | Unretarded Preparation | | |
|---|---|---|---|
| Constituents | mg | mg | mg |
| 1. Endralazine mesylate | 3.393 | 6.785 | 13.57 |
| 2. Calcium sulphate dihydrate | 85.807 | 82.415 | 75.63 |
| 3. Corn Starch | 75 | 75 | 75 |
| 4. Magnesium stearate | 0.8 | 0.8 | 0.8 |
| | 165 mg | 165 mg | 165 mg |

-continued

The constituents are mixed together and filled into capsules of size No.3 (Parke Davis).

The unit dosage forms of the above examples 1 and 2 are active in the method of the invention when given to provide a daily dosage of 10 to 100 mg or 10 to 50 mg endralazine.

If desired unit dosage forms containing larger amounts of endralazine may be made in analogous manner.

What I claim is:

1. A method for the prophylaxis of inflammatory, degenerative or proliferative arterial disease which method comprises orally administering to a subject in need of such treatment an effective amount of endralazine.

2. A method according to claim 1 for the prophylaxis of polyarteritis nodosa.

3. A method according to claim 1 for the prophylaxis of arteriosclerosis.

4. A method according to claim 1 wherein endralazine is administered at a daily dosage of from 50 to 600 mg.

5. A method according to claim 4 wherein endralazine is administered at a daily dosage of from 50 to 300 mg.

6. A method according to claim 4 wherein endralazine is administered in unit dosage form containing from 2 to 300 mg of endralazine.

7. A method according to claim 4 wherein endralazine is administered in unit dosage form containing from 12 to 150 mg of endralazine.

8. A method for the prevention of progressive inflammatory, degenerative or proliferative damage in arteries in a subject in need of such treatment, which method comprises orally administering an effective amount of endralazine.

9. A method according to claim 8 for the prevention of the progressive development of arterial lesions.

10. A method according to claim 8 wherein endralazine is administered at a daily dosage of from 50 to 600 mg.

11. A method according to claim 10 wherein endralazine is administered at a daily dosage of from 50 to 300 mg.

12. A method according to claim 10 wherein endralazine is administered in unit dosage form containing from 2 to 300 mg of endralazine.

13. A method according to claim 10 wherein endralazine is administered in unit dosage form containing from 12 to 150 mg of endralazine.

* * * * *